United States Patent
Dyckman et al.

(10) Patent No.: US 6,768,031 B2
(45) Date of Patent: Jul. 27, 2004

(54) PROCESS AND CATALYST FOR PRODUCING P-CUMYLPHENOL

(75) Inventors: Arkady Samuilovich Dyckman, Saint Petersburg (RU); John William Fulmer, Mt. Vernon, IN (US); Boris V. Krasy, Saint petersburg (RU); Viktor Vladimirovich Pinson, Saint Petersburg (RU); Yury Alekseevich Shavandin, Saint Petersburg (RU); Genrikh Petrovich Yavshits, Saint Petersburg (RU); Andrey Vladimirovich Zinenkov, Saint Petersburg (RU)

(73) Assignee: General Electric Company, Schenectady, NY (US)

( * ) Notice: Subject to any disclaimer, the term of this patent is extended or adjusted under 35 U.S.C. 154(b) by 2 days.

(21) Appl. No.: 10/357,008

(22) Filed: Feb. 3, 2003

(65) Prior Publication Data

US 2003/0158451 A1 Aug. 21, 2003

(30) Foreign Application Priority Data

Feb. 8, 2002 (RU) ........................................ 2002103668

(51) Int. Cl.⁷ .............................................. C07C 39/12
(52) U.S. Cl. ........................................................ 568/744
(58) Field of Search ............................................ 568/744

(56) References Cited

U.S. PATENT DOCUMENTS

| | | |
|---|---|---|
| 2,441,408 A | 5/1948 | Goldblum |
| 2,734,085 A | 4/1956 | Adams et al. |
| 2,744,143 A | 5/1956 | Filar |
| 2,910,511 A | 10/1959 | Joris |
| 2,992,169 A | 7/1961 | Gregory et al. |
| 3,331,879 A * | 7/1967 | Leston ..................... 568/794 |
| 3,335,070 A | 8/1967 | Adams |
| 3,437,699 A | 4/1969 | Flickinger |
| 3,466,260 A | 9/1969 | Bostian et al. |
| 3,545,653 A | 12/1970 | Larson |
| 3,692,845 A | 9/1972 | Cheema et al. |
| 3,862,244 A | 1/1975 | Genod et al. |
| 3,931,339 A | 1/1976 | Cooke |
| 3,965,187 A | 6/1976 | Little et al. |
| 4,092,360 A | 5/1978 | Van Peppen et al. |
| 4,251,325 A | 2/1981 | Marsh et al. |
| 4,298,765 A | 11/1981 | Cochran et al. |
| 4,334,107 A | 6/1982 | Van Peppen |
| 4,409,412 A | 10/1983 | Haag et al. |
| 4,906,791 A * | 3/1990 | Imanari et al. ............. 568/744 |
| 4,973,766 A | 11/1990 | Penzo et al. |
| 5,091,058 A | 2/1992 | Davie |
| 5,185,475 A | 2/1993 | Kissinger |
| 5,262,016 A | 11/1993 | Lorenzoni et al. |
| 5,264,636 A | 11/1993 | Shirahata et al. |
| 5,304,689 A | 4/1994 | Kissinger |
| 5,414,154 A | 5/1995 | Jenczewski et al. |
| 5,491,268 A | 2/1996 | Cipullo |
| 5,502,259 A | 3/1996 | Zakoshansky et al. |
| 5,510,543 A | 4/1996 | Fulmer et al. |
| 6,066,767 A | 5/2000 | Zakoshansky et al. |
| 6,201,157 B1 | 3/2001 | Keenan |
| 6,326,328 B1 | 12/2001 | Matsuzawa |
| 6,448,453 B1 | 9/2002 | Oberholtzer et al. |

FOREIGN PATENT DOCUMENTS

| | | |
|---|---|---|
| RU | 2058189 C1 | 4/1996 |
| RU | 1559494 A1 | 2/1997 |

OTHER PUBLICATIONS

Abstract for SU 1559494 from Derwent, Feb. 10, 1997, Russian Federation.

Abstract for RU 2058189 from Derwent, Apr. 20, 1996, Russian Federation.

J.C. Yori, M.A. D'Amato, G. Costa and J.M. Parera, Journal of Catalysis 153, 218–223 (1995).

U.S. application Ser. No. 09/683,190, filed Nov. 29, 2001 (Docket No. 08CL05994–1), System and Method for Purifying Cumene Hydroperoxide Cleavage Products, Fulmer et al.

* cited by examiner

Primary Examiner—Michael L. Shippen

(57) ABSTRACT

The specification provides a method for producing p-cumylphenol phenol by reacting phenol with α-methylstyrene in the presence of a highly efficient heterogeneous aluminum zirconium catalyst.

4 Claims, No Drawings

PROCESS AND CATALYST FOR PRODUCING P-CUMYLPHENOL

The present application is a U.S. non-provisional application based upon and claiming priority from Russian Application No. 2002103668, with a filing date of Feb. 8, 2002, which is hereby incorporated by reference.

BACKGROUND

This invention relates to the area of chemistry and petrochemistry, more precisely to a process for producing p-cumylphenol (PCP) by means of catalytic alkylation of phenol with α-methylstyrene (AMS).

p-Cumylphenol is widely used in producing effective stabilizers for fuels, oils, polymers, and rubbers.

Processes are known for producing p-cumylphenol using homogeneous acidic catalysts, such as strong mineral acids: sulfuric, oxalic, phosphoric, etc. [a) Kumok, Gurvich, Stiskin, Grinberg. *Zh. Vses. Khim. Obshchestva im. Mendeleeva* 17:4.460–462 (1972); b) U.S. Pat. No. 2,444,1408 (1948); c) U.S. Pat. No. 2,751,437 (1950)]. The disadvantages of this process are typical for the use of homogeneous catalysts. These are the low selectivity of the process, the difficulty of separating the catalytic complex from the reaction products, and ecological problems connected with the use of strong acids.

The indicated disadvantages are not present in the process for producing p-cumylphenol which uses heterogeneous catalysts, for example based on synthetic zeolites of the type of dealuminated mordenite or zeolites of the ZSM family, which are prepared with or without a binder and with the addition of promoter metals or without additives [U.S. Pat. No. 4,409,412 (1982)]. The disadvantage of using catalysts of this type is their insufficient activity and increased formation of side products. For example, when PCP is made by this method, dimer side products are also produced. Specifically, when this reaction is carried out at a temperature of 100° C., a raw material volumetric feed rate of 1 $h^{-1}$, using dealuminated mordenite as the catalyst, the content of the end product PCP in the catalysis product is 12–13% by mass, with the dimer content being greater than 4% and the o-cumylphenol content being 0.5–0.7% (wherein the diner and o-cumylphenol content is greater than 4.5%). When a sample of TsVM zeolite (a member of the ZSM-5 family) is used as catalyst quality of end product PCP is 11–12%, the dimer content is 0.6–0.7%, the o-cumylphenol content is about 2.2%, and the total content of dimer and o-cumylphenol is greater than 2.8%. (more than 2.8%), respectively.

In another known process for producing PCP, an ion-exchange resin of the type of Amberlyst in the hydrogen form is used as the catalyst [U.S. Pat. No. 5,185,475 (1993) prototype].

At a temperature of 80–110° C., under atmospheric pressure, and with a raw material volume feed rate of 1.0 $h^{-1}$, the content of PCP in the catalysis product is 16.2–16.5%, the content of dimers is around 0.3–0.5%, and the content of o-cumylphenol is 4.4% (the total of the latter two is greater than 4.6%). The disadvantages of the PCP synthesis process using ion-exchange resins as catalyst which is proposed as a prototype are as follows:

increased content of side products (o-cumylphenol and dimers);

insufficient activity of the catalyst;

low thermal stability of the catalyst, lowering its service life;

difficulty of regenerating the catalyst;

necessity of additional purification of the reaction products on alkaline sorbents to remove acidic components which are washed out of the catalyst.

The goal of this invention is to increase the activity and selectivity and to simplify the technology of the process for producing p-cumylphenol.

SUMMARY

The indicated goal is achieved by alkylating phenol with α-methylstyrene using a heterogeneous acidic aluminum zirconium catalyst at a temperature of 80–110° C. Also, a relative raw material volumetric feed rate must be maintained through the catalyst bed as necessary to provide a space velocity of 1–3 $h^{-1}$ (hereinafter referred to as a "volume feed rate").

The catalyst represents a mixture of aluminum oxide and zirconium oxide promoted by sulfate, with the total content of aluminum and zirconium sulfates being from 5 to 15% by mass (calculated on the basis of $SO_4$ ions) and the total content of aluminum oxide and sulfate being 5–30% by mass (calculated on the basis of $Al_2O_3$).

DETAILED DESCRIPTION

As a rule, aluminum oxide carriers of catalysts are prepared by precipitation of aluminum hydroxide from a solution of sodium aluminate using concentrated nitric acid at a pH of 8.7–8.9 in two streams: "cold" precipitation at 18–20° C. and "hot" precipitation at 100–120° C. Mixing these streams in different proportions makes it possible to regulate the quality of the product. The resulting mass of aluminum hydroxide is washed of sodium ions, plasticized, peptized, and molded into granules of a given size in screw extruders [USSR patent no. 1559494 (1986), Russian Federation patent no. 2058189, published in *Biulleten izobretenii* [Russian Patent Office Journal] no. 11 on Apr. 20, 1996].

Aluminum zirconium catalysts used for various syntheses are prepared by the process of precipitating zirconium oxychloride ($ZrOCl_2 \cdot 8H_2O$) with an aqueous ammonia solution and then drying the resulting precipitate and treating it with 1 N sulfuric acid. For molding into granules the sulfonated powdered zirconium oxide is mixed with aluminum hydroxide, which is used as a binder [*J. Catal.* 153:218–233 (1955)].

For example, a process is known of preparing an aluminum zirconium catalyst for isomerization of paraffin hydrocarbons [U.S. Pat. No. 6,326,328 (2001)]. The indicated process involves taking a mixture of powdered zirconium and aluminum hydroxides with the addition of a sulfonating agent—ammonium sulfate salts, mixing it, extruding it, and roasting the resulting granules at 600° C. Aluminum hydroxide or hydrated aluminum hydroxide are used as a binder. However, a catalyst prepared according to this process is not suitable for producing PCP, since it does not have sufficient activity.

The process for preparing the proposed composition of the p-cumylphenol synthesis catalyst by means of alkylating phenol with α-methylstyrene includes stages of precipitating zirconium hydroxide, mixing zirconium and aluminum hydroxides, sulfating, hydroxides, peptizing the electrolyte solution, screw extrusion of the catalyzed mass, and heat treatment. The starting aluminum compound that is used is aluminum hydroxide, consisting of boehmite and pseudo-boehmite in a mass ratio of 1:3 to 3:1 (calculated on the basis of $Al_2O_3$). Sulfuric acid is used as the sulfating and peptizing agent.

The essential characterizing features of the proposed process for preparing the catalyst are the use of a mixture of boehmite and pseudoboehmite in the indicated ratio at the stage of preparing aluminum hydroxide, and also using an aqueous sulfuric acid solution at the stage of sulfation and peptization of the catalyzed mass. The catalyst produced according to the proposed process based on sulfated aluminum and zirconium oxides can be regenerated both by means of treatment with heated gas (nitrogen) and by means of washing with a solvent, for example phenol.

This catalyst is significantly cheaper than ion-exchange resins and, as will be shown in below in the examples, has high activity and selectivity in the proposed process. We are not aware of processes for preparing aluminum zirconium catalysts of the proposed composition.

The industrial applicability of the proposed catalyst for the synthesis of p-cumylphenol by alkylation of phenol with α-methylstyrene and the process of preparing it are confirmed by the following examples.

EXAMPLE 1 a) Preparation of Catalyst 431 g of the salt $ZrOCl_2.8H_2O$ are dissolved in 5.2 L of distilled water. 332 mL of $NH_4OH$ solution having a concentration of about 25% is dripped into the resulting solution over 20 minutes. The resulting precipitate is filtered off and washed with water on a Büchner funnel to remove ammonium chloride. The resulting washed precipitate is dried in a drying cabinet at 110° C. for 24 hours. The dried precipitate is ground in a mill, and the resulting fine powder is sifted in a 180 μm sieve. The mass of the powder is 190 g or 147 g, calculated on the basis of $ZrO_2$.

To sulfate the powder, it is treated with 1.14 L of 1 N sulfuric acid solution for 1 hour. Then, the resulting mixture is filtered to remove excess solution, and the product is dried at 110° C. (10 h) and is further used for molding.

To produce pseudoboehmite, 3 L of a 100 g/L sodium aluminate solution is used. The precipitation is performed by simultaneously pouring together the indicated aluminate solution and a 60% solution of nitric acid (yield: 1.8 L) at a temperature of 20–25° C. and at a pH in the range 9.1 to 9.5 over the course of 2 hours. After the solutions have been completely poured in, the suspensions are stabilized by boiling (102–105° C.) at a pH that is kept constant in the range 9.1–9.3 by adding sodium aluminate solution. The product is a suspension of glassy precipitate of pseudoboehmite containing 300 g of $Al_2O_3$.

To produce boehmite, 1 L of a 100 g/L sodium aluminate solution is used. The precipitation is performed by simultaneously pouring together the indicated aluminate solution and a 60% solution of nitric acid (yield: 0.7 L) at a temperature of 102–105° C. (when boiling) and at a pH in the range 8.5 to 8.9 over the course of 2 hours. The product is a suspension of honey-like precipitate of boehmite containing 100 g of $Al_2O_3$.

The resulting suspensions of pseudoboehmite and boehmite are combined and washed on a Büchner funnel to remove the contaminating sodium nitrate salt. The washed precipitate is dried at 110° C. for 10 hours and ground into a fine powder all of which passes through a sieve having 0.25 mm openings. The calcining loss when the resulting dried mixed aluminum hydroxide powder is roasted at 850° C. is 24.6% by mass. The ratio of boehmite to pseudoboehmite in the aluminum hydroxide powder is 1:3, calculated on the basis of $Al_2O_3$.

After that, the powdered sulfated zirconium hydroxide is mixed with 83.6 g of powdered aluminum hydroxide in a Werner & Pfleiderer Z blade mixer, the solution is peptized with sulfuric acid solution (3.8 mL of 60% solution), and small portions of around 250 mL of water are added, bringing the moisture content (calcining loss) of the mass to 55% by mass. The resulting mass is molded in a screw extruder through a die having a hole diameter of 2.0 mm. The extrudates are dried for 8 hours at 110° C. and then roasted in a stream of dried air for 4 hours at 630° C.

Gross composition of the finished catalyst: 66.2% by mass of $ZrO_2$; 30% by mass of $\gamma$-$Al_2O_3$; 5.0% by mass of S. The total content of aluminum and zirconium sulfate in the catalyst was 15.0% (calculated on the basis of S04), and the total content of aluminum oxide and sulfate was 30% by mass (calculated on the basis of $Al_2O_3$).

b) Test of Catalyst

The process of alkylating phenol by α-methylstyrene on the resulting catalyst is carried out at a temperature of 80° C. and with a raw material volume feed rate of 1 $h^{-1}$.

The raw material used is a mixture of phenol, cumene, and α-methylstyrene having the composition (in mass %): cumene—45%; phenol—45%; and α-methylstyrene—10%.

The yield of the catalysis product was 99.89%, and its composition was as follows (in mass %): cumene—46.68%; α-methylstyrene—0.05%; phenol—34.57%; PCP—16.61; o-cumylphenol—1.19; and dimers—0.9%.

After p-cumylphenol is isolated by distillation, the product has the following composition (in mass %): p-cumylphenol—98.2%; o-cumylphenol—1.4%; dimers—0.16%; α-methylstyrene and others—0.24%.

The composition of the catalysis product was determined by gas/liquid chromatography on a "Kristall 2000M" chromatograph with a capillary column 25 m long using OV-1 as the stationary phase.

EXAMPLE 2 a) Preparation of Catalyst

The catalyst is prepared as in Example 1, but the ratio of boehmite to pseudoboehmite (calculated on the basis of $Al_2O_3$) in the mixed powdered aluminum hydroxide is 3:1. The zirconium hydroxide precipitate is sulfated with 380 mL of sulfuric acid solution. The quantity of mixed powdered aluminum hydroxide taken for mixing with the powdered sulfated zirconium hydroxide is 13.9 g. The remaining parameters are the same as in Example 1.

The total content of aluminum and zirconium sulfates in the resulting sample of roasted (finished) catalyst, calculated on the basis of $SO_4$, was 5.0% by mass, and the total content of aluminum oxide and sulfate was 5% by mass, calculated on the basis of $Al_2O_3$.

b) Test of Catalyst

The resulting catalyst is tested under the conditions of Example 1 at a temperature of 10° C. and a raw material volume feed rate of 3 $h^{-1}$. The resulting catalysis product has the following composition (in mass %): cumene—46.13%; α—ethylstyrene—0.04%; phenol—34.6%; PCP—17.17%; o-cumylphenol—1. 10%; and dimers—0.5%.

Thus, the proposed aluminum zirconium catalyst, produced by the proposed process, makes it possible to carry out the process of synthesizing p-cumylphenol by alkylation of phenol with α-methylstyrene at a temperature of 80–110° C. and a raw material volume feed rate of 1–3 $h^{-1}$ with extremely high efficiency: the content of the end product PCP in the catalysis product is more than 17% by mass, with a low percentage of side products formed—o-cumylphenol and dimers up to 2% by mass.

The catalyst worked 500 hours without a noticeable reduction in its activity or selectivity.

What is claimed is:

1. A process for producing p-cumylphenol which process comprises reacting phenol with α-methylstyrene in the presence of an acidic aluminum zirconium catalyst at a temperature above 80° C., and subsequently isolating the p-cumylphenol from the catalysis product by distillation, wherein the catalyst is a mixture of aluminum and zirconium oxides and sulfates having a total content of aluminum and zirconium sulfate of from 5 to 15% by mass (calculated on the basis of $SO_4$ ions) and a total content of aluminum and oxide and sulfate of 5–30% by mass (calculated on the basis of $Al_2O_3$) and raw material volume feed rate of the phenol and α-methylstyrene is 1–3 $h^{-1}$.

2. The process according to claim 1, wherein the catalyst consists essentially of a mixture of aluminum and zirconium oxides and sulfates.

3. The process according to claim 2, wherein the aluminum zirconium catalyst is prepared by a process comprising the step of treating a mixture of aluminum hydroxide and zirconium hydroxide with aqueous sulfuric acid, wherein the aluminum hydroxide is a mixture of boehmite and pseudo boemite in a mass ratio of from 1:3 to 3:1.

4. The process according to claim 3, wherein the aluminum zirconium catalyst is prepared by a process comprising the steps of:

a) precipitating zirconium hydroxide, b) mixing aluminum hydroxide and the zirconium hydroxide, c) sulfating the zirconium hydroxides by treatment with aqueous sulfuric acid, d) peptizing the aluminum hydroxide and the sulfated zirconium hydroxide with aqueous sulfuric a acid, e) next screw extruding the peptized mixture of hydroxides and f) heat treating the extruded mixture.

* * * * *